United States Patent [19]

McClure

[11] Patent Number: 5,623,936
[45] Date of Patent: Apr. 29, 1997

[54] IMPLANTABLE MEDICAL DEVICE HAVING MEANS FOR DISCRIMINATING BETWEEN TRUE R-WAVES AND VENTRICULAR FIBRILLATION

[75] Inventor: Kelly H. McClure, Simi Valley, Calif.

[73] Assignee: Pacesetter, Inc., Sylmar, Calif.

[21] Appl. No.: 567,658

[22] Filed: Dec. 5, 1995

[51] Int. Cl.$^6$ .............................. A61B 5/046; A61N 1/39
[52] U.S. Cl. .............................. 128/705; 607/5
[58] Field of Search .................. 128/705, 708; 607/5

[56] References Cited

U.S. PATENT DOCUMENTS

| | | | |
|---|---|---|---|
| 3,858,034 | 12/1974 | Anderson | 235/151.3 |
| 4,000,461 | 12/1976 | Barber et al. | 324/102 |
| 4,129,133 | 12/1978 | Irnich et al. . | |
| 4,181,133 | 1/1980 | Kolenik et al. . | |
| 4,280,502 | 7/1981 | Baker et al. . | |
| 4,296,755 | 10/1981 | Judell | 128/705 |
| 4,393,877 | 7/1983 | Imran et al. | 128/705 |
| 4,458,692 | 7/1984 | Simson | 128/705 |
| 4,478,224 | 10/1984 | Bailey | 128/708 |
| 4,493,325 | 1/1985 | Hartlaub et al. . | |
| 4,552,154 | 11/1985 | Hartlaub | 128/702 |
| 4,630,204 | 12/1986 | Mortara | 364/417 |
| 4,686,989 | 8/1987 | Smyth . | |
| 4,790,317 | 12/1988 | Davies . | |
| 4,830,006 | 5/1989 | Haluska et al. . | |
| 4,880,004 | 11/1989 | Baker et al. . | |
| 4,880,005 | 11/1989 | Pless et al. . | |
| 4,905,708 | 3/1990 | Davies | 128/705 |
| 4,969,465 | 11/1990 | Pless et al. . | |
| 5,103,822 | 4/1992 | Duncan . | |
| 5,161,527 | 11/1992 | Nappholz et al. . | |
| 5,188,105 | 2/1993 | Keimel . | |
| 5,205,283 | 4/1993 | Olson . | |
| 5,217,021 | 6/1993 | Steinhaus et al. | 128/702 |

OTHER PUBLICATIONS

UK Patent Application No 8526417, Filed Oct. 25, 1985.

Primary Examiner—William E. Kamm
Assistant Examiner—George R. Evanisko

[57] ABSTRACT

An improved "VF immune" cardiac event detector for an implantable medical device consists of high-frequency and a low-frequency delta converters coupled to an intracardiac signal. The high-frequency delta converter is tuned to be responsive to R-waves and VF waveforms. However, the low-frequency delta converter is tuned to be responsive only to VF waveforms. By monitoring the difference between the outputs of the high-frequency and the low-frequency delta converters, the system can effectively discriminate between "true" R-waves and VF waveforms.

38 Claims, 7 Drawing Sheets

IMPLANTABLE MEDICAL DEVICE HAVING MEANS FOR DISCRIMINATING BETWEEN TRUE R-WAVES AND VENTRICULAR FIBRILLATION

FIELD OF THE INVENTION

The present invention relates to an implantable medical device having an improved cardiac event detection system, and more particularly to a system for accurately discriminating between true R-waves (i.e. of sinus origin) and ventricular fibrillation waveforms that may be present.

BACKGROUND OF THE INVENTION

Every modern-day implantable pacemaker includes a sensing circuit for detecting cardiac events (herein-after referred to as an "event detector"), whether the activity of one or both chambers of the heart is sensed. The electrical cardiac signal, as recorded inside the heart, is called an intracardiac electrogram, IEGM, (or simply, an electrogram, EGM) and is a very rapid, relatively large signal. The most rapid portion of this signal is called the intrinsic deflection, and this is what the pacemaker senses. The pacemaker can sense the intrinsic deflection portion of one or both of the atrial or ventricular electrogram (EGM) from within the heart. The atrial EGM coincides with the P-wave of the surface ECG, while the ventricular EGM coincides with the R-wave of the surface ECG. For purposes of simplicity and consistency with common usage, the terms P-wave and R-wave, as used herein, are synonymous with the intrinsic deflection portion of the atrial and ventricular electrograms, respectively.

In practice, the cardiac signal is amplified within the event detector by a sense amplifier, and the sensitivity level of the pacemaker is proportional to the gain of the sense amplifier. A cardiac event is sensed when an amplified cardiac signal from the sense amplifier exceeds a threshold level. The sensitivity level of the pacemaker and the threshold level are selected such that only the amplified waves of interest (e.g., the R-waves or P-waves) exceed the threshold level. In response to the amplified EGM signal exceeding the threshold level, the event detector generates an event detection signal. Various methods and apparatus for selecting the sensitivity level and the threshold level are known in the art, including manual physician-adjusted methods and apparatus, and sophisticated microcontroller-based methods and apparatus.

Problematically, however, from the onset of ventricular fibrillation (VF), the amplified cardiac signal will typically begin to exceed the threshold value in a rapid and unpredictable manner due to the rapid, unsynchronized electrical activity in the heart that accompanies VF. Such rapid and unpredictable behavior in the cardiac signal is referred to herein as a VF waveform. In response to the VF waveforms, the event detector will rapidly generate the event detection signal even though no true R-waves are present in the IEGM. That is, the threshold crossings by the VF waveform do not coincide with a synchronous contraction of the heart muscle. Rather than being a wavefront of a global cardiac depolarization (and corresponding contraction), the VF waveform is caused by a relatively small number of cells adjacent to the sensing lead.

Heretofore, various attempts have been made to distinguish between actual R-waves and signals corresponding to VF. The most primitive of such systems, referred to herein as "rate detection systems", simply classify event detection signals that exceed a tachycardia rate threshold (e.g., 200 bpm) as a tachyarrhythmia. U.S. Pat. Nos. 4,181,133; 4,280,502; 4,686,989; 4,969,465; 5,103,822; and 5,205,283; incorporated herein by reference, show such rate detection systems.

Another attempt to distinguish R-waves from VF waveforms (and tachyarrhythmias) is shown in U.S. Pat. No. 4,880,005 ('005 Patent), incorporated herein by reference. In accordance with the '005 Patent, various factors are monitored, such as the rate of detected signals, the stability of such rate, the suddenness in onset of increased rate, and the sustainment of high rate.

Alternately, some methods analyze the morphology (or shape) of the EGM waves to identify or predict VF or tachyarrhythmia. (See, e.g., U.S. Pat. Nos. 4,442,459; 4,552,154; and 4,630,204; incorporated herein by reference.)

Other methods employ complex algorithms in order to try to distinguish between R-waves and VF waveforms or tachyarrhythmias (e.g., U.S. Pat. Nos. 4,493,325; 4,830,006; 4,880,004; 4,905,708; 5,188,105; and 5,217,021; incorporated herein by reference).

For example, the frequency components of the IEGM may be analyzed during a window of time during which the R-wave is expected to occur. In the event that the R-wave is present during the window of time, very high-frequency components will be observed in the IEGM due to the high-frequency content of the R-wave. However, if instead the VF waveform is present in the IEGM during the window of time, relatively low-frequency components will be observed in the IEGM. Using mathematical analysis (e.g., the Fast Fourier Transform, FFT) or other frequency-based algorithm, it is possible to distinguish between an IEGM representing sinus cardiac rhythm, and an IEGM representing ventricular fibrillation.

Another method used to detect VF or VT is the monitoring of several locations in the heart for electrical activity. When R-waves are generated, the electrical activity will occur in the several locations in a specific sequence that is repeated each time the heart beats. At the onset of VF, this sequence will change or become unpredictable, thus indicating that any generated event detection signals are due to VF (see, e.g., U.S. Pat. No. 4,790,317, incorporated herein by reference).

One final example of a method used to distinguish between event detector outputs is shown in U.S. Pat. No. 5,161,527 ('527 patent), incorporated herein by reference. The '527 patent uses at least one metabolic indicator sensor to determine not only the appropriate rate for bradycardia pacing, but also to distinguish physiological from pathological intrinsic cardiac rhythms.

Problematically, each of the methods set forth in the aforecited patents inherently must work backwards to discriminate between event detection signals that correspond to R-waves from those that are a result of VF waveforms or ventricular tachycardia (VT).

What is needed, therefore, is an improved R-wave event detection system which can discriminate between "true" R-waves (i.e., of sinus origin) from ventricular fibrillation.

SUMMARY OF THE INVENTION

The present invention provides a cardiac event detector for use within an implantable pacemaker to detect R-waves in the intracardiac electrogram signal (referred to hereinafter simply as the IEGM), wherein such detection discriminates "true" R-waves from ventricular fibrillation based on the frequency content of the IEGM input signal, without requiring an FFT or other complex transformation.

Unlike the above-mentioned methods, which detect R-waves by generating event detection signals in response to both R-waves and VF waveforms, the present invention generates a detection signal only in response to R-waves, and is substantially insensitive to VF waveforms.

Advantageously, the present invention achieves this by essentially processing the IEGM through both a high-frequency and a low-frequency delta converter and then observing the difference therebetween. The high-frequency delta converter responds quickly to R-waves and VF waveforms. Whereas the low-frequency converter responds slowly to the R-wave, but adequately to the slow-moving VF waveform. The present invention is based on the premise that a large difference between the high-frequency converter and the low-frequency converter will indicate a true R-wave and that ventricular fibrillation is present when the high-frequency and low-frequency delta converters contain the same magnitude (within some tolerance).

In order to understand the present invention, it would be helpful to have a basic understanding of the operation of a delta converter and the factors to consider when designing a delta converter.

Briefly, a delta converter generates a "delta signal" which indicates whether an input signal, is increasing or decreasing, during a set of clock cycles (or clock phases). This is achieved by comparing a current input signal to a previous input signal. In the event the current input is greater than the previous input signal, an increase bit is generated at the output of the delta converter. In the event that the current input signal is less than the previous input signal, a decrease bit is generated at the output of the delta converter.

However, in order for the current input signal to be considered "greater than" or "less than" the previous input signal, the previous input signal must differ from the previous input signal by at least one step (i.e., current>(previous+1 step), or previous>(current+1 step)). A step is a predetermined voltage difference defined within the delta converter.

In the event that the current input signal exceeds the previous input signal by less than one step (or in the event the previous input signal exceeds the current input signal by less than one step), the delta converter will generate either an increase bit, a decrease bit, or a neutral bit, depending on the particular delta converter utilized.

For example, the one type of delta converter may generate an increase bit in response to the current input signal being within one step of the previous input signal if the delta converter generated a decrease bit during the previous clock cycle, and visa versa. Thus, this exemplary type of delta converter will alternate between generating an increase bit and generating a decrease bit in response to an input signal that is relatively flat, i.e., that does not change by more than one step per clock cycle.

A delta converter accumulates the increase bits and the decrease bits during a delta cycle (e.g., eight clock cycles). In response to the accumulated bits, the delta converter generates a "delta signal", which is a signed signal indicative of the increase and decrease bits accumulated during the delta cycle. Thus, the delta signal is indicative of the overall change in the input signal during the delta cycle.

In general, there are three factors that can cause the delta signal to produce an output which is not indicative of the overall change in the input signal over the delta cycle. First, if the step is too large (i.e., larger than the changes in the input signal), then a delta converter may (e.g., as in the exemplary delta converter above) alternate between generating the increase bit and the decrease bit. As a result, the delta signal (which will be indicative of approximately equal numbers of increase bits and decrease bits) will indicate a reactively flat input signal, even though the input signal may be changing significantly during each delta cycle (but by less than one step per clock cycle).

Second, if the step is too small, a delta converter will not be able to "catch up" to the input signal. This is because each increase bit can represent only a one step increase, and visa versa for each decrease bit. For example, if the input signal is increasing at a rate of two steps per clock cycle the delta converter will generate an increase bit each clock cycle. However, the delta signal, being indicative of the increase bits accumulated during the delta cycle, will indicate that the input signal has increased by only one step per clock cycle. Over several delta cycles, therefore, the change in the input signal indicated by the delta signal can differ greatly from (i.e., lag behind) the actual change in the input signal over the several delta cycles.

Third, if the clock rate is too slow (i.e., if the clock cycles are too long), the delta converter will also not be able to "catch up." Using the above example, wherein the input signal is increasing by two steps per clock cycle, suppose that the step size were doubled, and the length of the clock cycle were doubled. The input signal would thus still be increasing at a rate of two steps per clock cycle, and the above-described problem of delta signal lag would likewise occur even though the step size had been doubled. Problematically, however, any increase in clock rate causes increased battery drain within the pacemaker. Therefore, the clock rate should be selected to be as slow as possible, taking into consideration the above-described problem caused by a clock rate that is too slow.

The present invention makes advantageous use of the above characteristics of a delta converter. By "tuning" a first delta converter using a prescribed step and a first clock signal (a high-frequency clock signal), the first delta converter can be made to generate a first delta signal that is indicative of the change in a fast input signal (e.g., an R-wave) over the delta cycle. Thus, the first delta converter can also be referred to as a high-frequency delta converter and is capable of accurately sampling R-waves and slower frequency VF waveforms.

A second delta converter is tuned using the prescribed step and a second clock signal (a low-frequency clock signal). The second delta converter will generate the second delta signal only when the slew rate of the input signal exceeds the slow VF slew rate, and will not generate the second delta signal when the faster slew rate of an R-wave is present. Thus, in response to the VF waveform, the low-frequency delta converter and the high-frequency delta converter generate the first and second delta signals that are substantially equal to one another; but in response to the R-wave, the low-frequency delta converter generates the second delta signal that is substantially smaller than the first delta signal generated by the high-frequency delta converter.

Note that the same result can be achieved using the first and second delta converter wherein each uses the same clock signal, but with different size steps. In this case, the first delta converter utilizes a large step, and the second delta converter utilizes a small step. The large step is sufficiently large enough to represent changes (or slew) in the input signal in response to the VF waveform and in response to the R-wave. The small step is sufficiently large enough to accurately represent changes (or slew) in the input signal in response to VF waveforms, but too small to represent increases (or slew) in the input signal caused by R-waves. The former approach, however, using differing clock signals, is described below by way of example.

The first and second delta signals are accumulated (or effectively integrated) in first and second counters that generate first and second integrated signals respectively. Periodically, the subtractor generates a difference signal that is indicative of the difference between the first and second integrated signals. In the presence of VF, the integrated signals will be substantially equal, because the first and second delta signals will by substantially equal, as explained above. Thus, the difference signal will be substantially zero when the VF waveform is present.

In contrast, the integrated signals will differ in response to the R-wave, because the first and second delta signals will differ, as explained above. Consequently, the difference signal will be non-zero when the R-wave is present.

The difference signal is applied to first and second comparators, the first comparing the difference signal to a high threshold signal and the second to a low threshold signal. In the event the difference signal exceeds either the high or low threshold signal, the first or second comparator, respectively, generates a high or low detect signal. The high threshold signal is typically a positive signal, and the low threshold signal is typically a negative signal. Thus, the high and low threshold signals define a window of signal levels that the difference signal can assume without the high or low detect signal being generated (as occurs when the VF waveform is in the input signal because the first and second integrated signals are substantially equal). When the difference signal is large (as occurs in response to the R-wave being in the input signal), either the high or low detect signal will be generated in response to the difference signal exceeding the high or low threshold signal, respectively. The high and low detect signals are coupled to an "OR" gate that generates a detection signal in response to the generation of the high and/or low detect signals.

Thus, the event detection signal is generated in response to the R-wave, but is not generated in response to the VF waveform.

In summary, the present invention can thus be characterized as an apparatus that includes: (1) a high-frequency delta converter, coupled to the IEGM signal, to produce a first delta signal; (2) a low-frequency delta converter, also coupled to the IEGM signal, to produce a second delta signal; (3) a first counter, coupled to the high-frequency delta converter, so as to integrate the first delta signal; (4) a second counter, coupled to the low-frequency delta converter, so as to integrate the second delta signal; (5) a subtractor for producing a difference signal between the first and second integrated signals; and (6) comparator circuitry for comparing the difference signal to a predetermined threshold and to produce an event detect signal when the threshold has been exceeded.

In an alternate embodiment, the present invention can be characterized as an improved ventricular fibrillation detector since a non-zero difference signal which occurs in the absence of true R-waves has shown to be a reliable indicator of the presence of a VF waveform.

In operation, the event detection signal is generated whenever the R-wave is present; the detection signal is not generated whenever the VF waveform is present.

The invention can also be characterized as a method having the following steps: (a) tuning a first delta converter to be responsive to both R-waves and VF waveforms; (b) tuning a second delta converter to be responsive only to VF waveforms; (c) receiving the intracardiac signal as inputs to both the first and the second delta converters and producing as an output a first and a second delta signal, respectively; (d) determining a difference signal based on the first and second delta signals; and (e) determining if the difference signal exceeds a predetermined threshold signal and producing an event detection signal thereof; whereby an event detection signal is not generated when the VF waveform is present in the intracardiac signal.

Note that the clock frequencies of the delta converters can be tuned such that the high-frequency converter is converting at a rate that produces the largest amplitude signal for the R-wave without oversampling; while the low-frequency converter can be tuned to not convert the rapid R-waves.

In this way, the detection signal is generated whenever a R-wave is present, and the detection signal is not generated whenever ventricular fibrillation waveforms are present. It should be apparent that ventricular fibrillation is present whenever the high-frequency and low-frequency delta converters contain the same magnitude (within some tolerance).

It is thus a feature of the present invention to provide a detection apparatus or method that detects an R-wave, whenever a true R-wave is present within the cardiac signal, but not to detect R-waves when ventricular fibrillation waveform is present.

It is another feature of the invention to provide such an apparatus and method that generates a detection signal in response to such R-waves and not to generate a detection signal in response to such ventricular fibrillation waveform.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate like components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
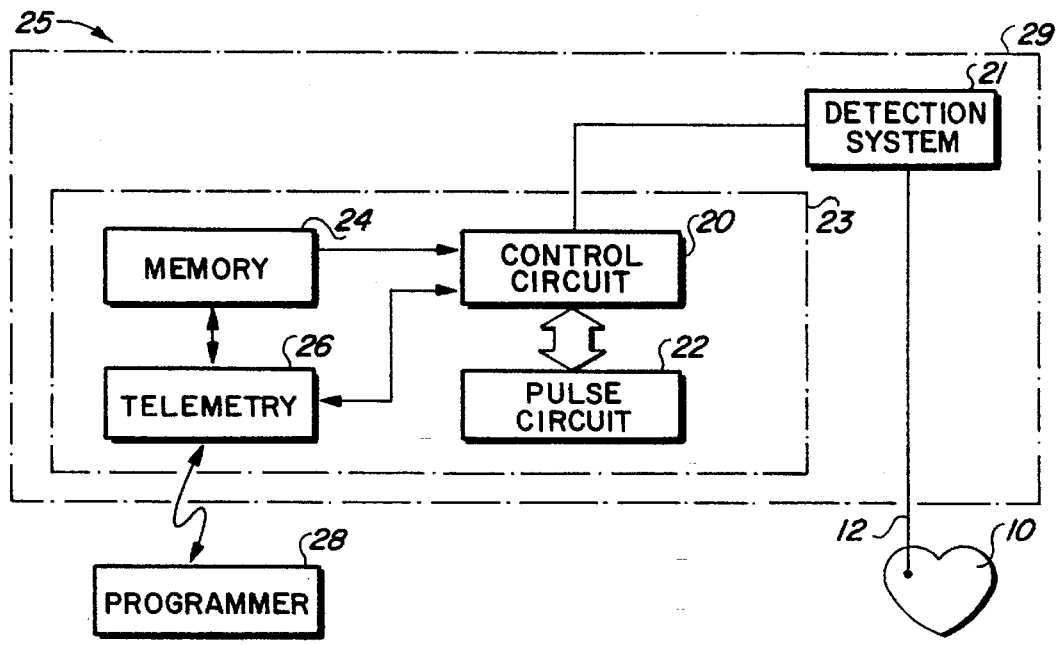
FIG. 1 is a block diagram of a cardiac pacemaker that utilizes the present invention as a cardiac event detector.

As shown in FIG. 1, a block diagram is shown of a typical cardiac pacemaker of the type with which the present invention can be utilized.

A cardiac event detector 21 and therapy circuitry 23 comprise, in combination, an implantable device 25 that is implanted into a patient and attached to a heart 10 of the patient via a lead 12. The lead 12 provides electrical communication between the implantable device 25 and the heart 10. Through the lead 12, intracardiac signals are communicated from the heart 10 to a cardiac event detector 21 within the implantable device 25. The implantable device 25 is housed in an implantable, hermetically sealed housing 29, as is known in the art of implantable electronic pacemakers.

The cardiac event detector 21 processes the intracardiac signal and generates at least one output signal. The output signal is coupled to the therapy circuitry 23, such as a cardiac pacemaker. The therapy circuit 23 controls the therapy delivered to the heart 10 (typically stimulation pulses) via the lead 12. Alternatively, a second lead may be used to deliver the desired therapy (e.g., as in dual-chamber stimulation systems) to the patient's heart 10.

By way of example, in FIG. 1, the therapy circuit 23 of the present invention comprises a cardiac pacemaker (hereinafter "cardiac pacemaker 23"). However, it should be understood that the present invention is suitable for use in an antitachycardia pacemaker, a cardioverter, an implantable monitoring device, a heart simulator, and a defibrillator.

The cardiac pacemaker 23 includes a control circuit 20, a pulse generation circuit 22, a memory 24, and a telemetry circuit 26. The control circuit 20 receives the output signal from the cardiac event detector 21 and, in response thereto, evaluates whether or not optimum therapy is being delivered to the heart 10. If the therapy being delivered is not optimum, the control circuit 20 makes adjustments, as required, and delivers a more optimum therapy to the heart 10. In general, the therapy delivered to the heart 10 may be repeatedly adjusted until optimum or near optimum therapy is delivered to the heart 10.

Figure 2:
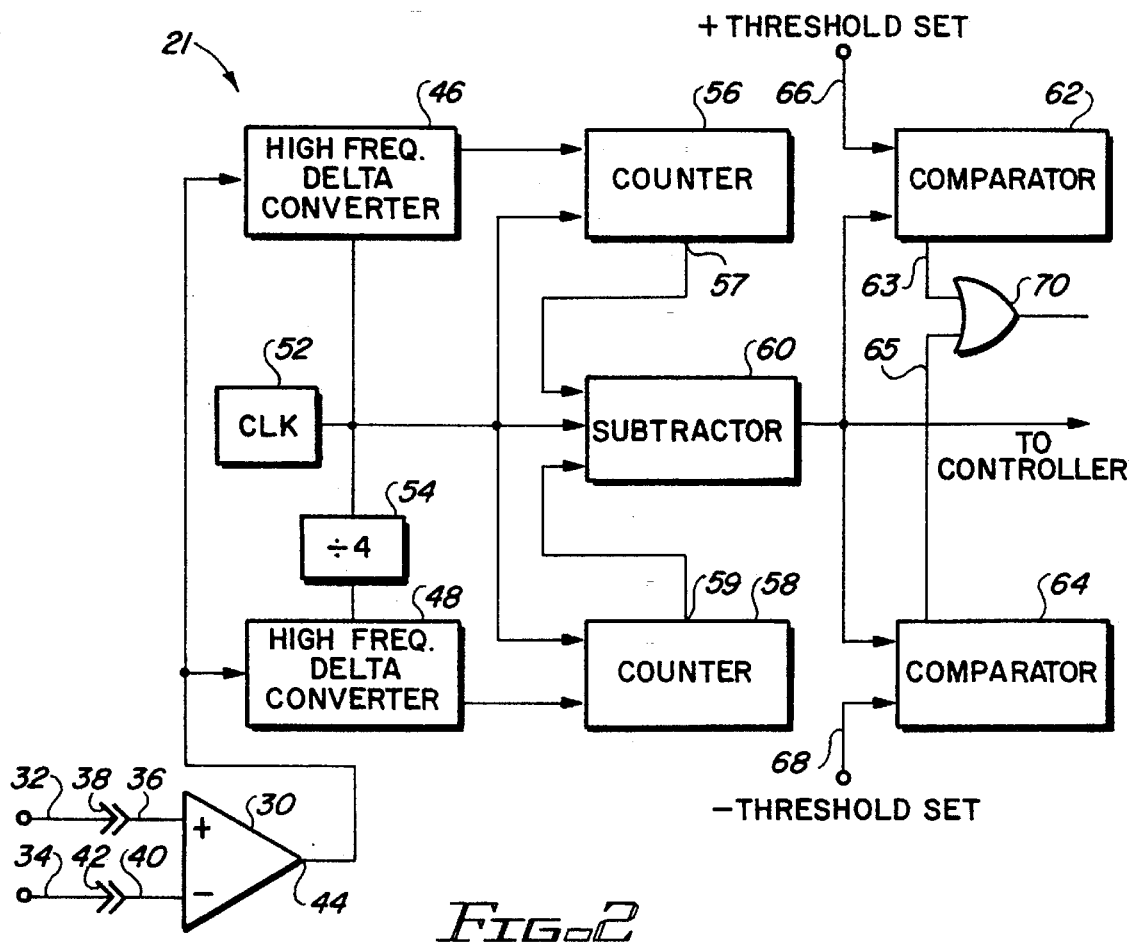
FIG. 2 is a block diagram of a cardiac event detector made in accordance with the present invention useable within the cardiac pacemaker shown in FIG. 1.

In FIG. 2, a block diagram is shown of a cardiac event detector 21 of the present invention. The lead 12 of FIG. 1 is coupled to an amplifier 30. The lead 12 contains at least one electrical conductor (e.g., a unipolar lead) and preferable two (e.g., a bipolar lead). At the distal end of the lead 12, a first conductor 32 is coupled to a tip (not shown) of the lead. At the proximal end of the lead 12, the first conductor 32 is coupled to the non-inverting input 36 of the amplifier 30 at a first connection point 38.

In a unipolar configuration, the inverting input 40 of the amplifier 30 is coupled to the housing (29 of FIG. 1) of the implantable device 25, which acts like a return electrode, at a second connection point 42. Thus, the voltage potential between the non-inverting input and the inverting input is the "unipolar" intracardiac signal.

In a bipolar configuration, the lead 12 includes a second conductor 34 coupled to a ring electrode (not shown). The second conductor 34 is coupled to the inverting input 40 of the amplifier 30 at the second connection point 42. The voltage potential between the non-inverting input and the inverting input is the "bipolar" intracardiac signal. Such unipolar and bipolar leads are known in the art of cardiac pacing.

Note that the present invention, in some embodiments, may comprise only one part of the cardiac event detector 21. Other parts may include filtering circuits, pre-amplifier circuits, ventricular fibrillation detectors, morphology detectors, or the like. Such other circuits and detectors are known in the art and are commonly included in cardiac event detectors 21 such as is shown in FIG. 1.

An output 44 of the amplifier 30 is coupled to two delta converters: a high-frequency delta converter 46 and a low-frequency delta converter 48. Delta converters suitable for use with the present invention are well known in the art. Operation of the delta converters is explained below in the discussion of FIG. 5. The delta converters 46, 48 receive an amplified IEGM signal from the amplifier output 44. The high-frequency delta converter 46 is coupled to a clock circuit 52 that generates a high-frequency clock signal having a frequency of between 1 and 32 kHz (e.g., 16 kHz). The high-frequency delta converter 46 is clocked by the high-frequency clock signal, in response to which, the high-frequency delta converter 46 has a high sampling rate (e.g., 2000 Hz).

The clock divider 54 generates a low-frequency clock signal, e.g., by dividing the first clock signal by four. The low-frequency delta converter 48 is clocked using the low-frequency clock signal and, consequently, has a low sampling rate (e.g., 500 Hz). Thus, the high-frequency delta converter 46 is clocked at a clock rate that is at least twice in frequency and preferably is approximately four times the clock rate at which the low-frequency delta converter 48 is clocked. This ratio may, however, be programmable and/or set to optimize the differences in the magnitude of the high-frequency delta converter and the low-frequency delta converter during normal sinus rhythm.

In response to the amplified IEGM signal and the high-frequency clock signal, the high-frequency delta converter generates a first delta signal in the form of a serial bit stream of between 250 to 8000 bits per second, bps (e.g., 8000 bps). Likewise, in response to the amplified IEGM signal, and the low-frequency clock signal, the low-frequency delta converter 48 generates a second delta signal in the form of a serial bit stream of between 50 to 2000 bps (e.g., 2000 bps).

As an alternative to the above-described delta converters, an analog to digital (A/D) converter coupled to a controller (a microcontroller or a microprocessor) can be used. Advantageously, this alternative may utilize an A/D converter and a controller that are otherwise utilized within the cardiac pacing system, e.g., as part of the control circuit 20 (FIG. 1). The A/D converter is coupled to the output 44 of the amplifier 30, and converts the output, which is an analog signal, to a digital signal. The digital signal is coupled to the controller. A control program within the controller performs the above-described functions of the delta converters in response to which the first and second delta signals are generated.

The first and second delta signals are coupled to first and second 8-bit counters 56, 58, respectively. The first and second 8-bit counters 56, 58 are clocked by the high-frequency clock signal, and serve to effectively integrate the first and second delta signals. The integrated first and second delta signals are represented at first and second outputs 57, 59, of the first and second 8-bit counters 56, 58, respectively, as first and second integrated signals. Alternatively, the controller (described above) may perform the functions of the counters in response to the control program, and generate the first and second integrated signals.

The first and second integrated signals are coupled to a subtractor 60 that generates a difference signal. The difference signal is an 8-bit signed signal that is indicative of the relative difference in magnitude between the first and second integrated signals. The subtractor 60 is also clocked by the high-frequency clock signal. Alternatively, the functions of the subtractor may be performed by the controller (described above) in response to the control program. When used, the controller generates the difference signal 108.

The difference signal 108 from the subtractor 60 is coupled to a first comparator 62. The first comparator 62 compares the difference signal to a high threshold signal (+THRESHOLD_SET) that is provided, e.g., by the control circuit 20 (FIG. 1). The high threshold signal may be one of the various control parameters stored in the memory 24. In the event that the difference signal 108 exceeds the high threshold signal, a high detect signal 63 is generated by the first comparator 62. The high threshold signal is a positive signal, and thus is exceeded when the difference signal 108 is positive in sign and of sufficient magnitude to exceed the high threshold signal.

The difference signal 108 from the subtractor 60 is also coupled to a second comparator 64. The second comparator 64 compares the difference signal 108 to a low threshold signal (-THRESHOLD_SET) that is provided, e.g., by the control circuit 20 (FIG. 1). The high threshold signal may also be one of the various control parameters stored in the memory 24. In the event that the difference signal 108 exceeds the low threshold signal, a low detect signal 65 is generated by the second comparator 64. The low threshold signal is a negative signal, and thus is exceeded when the difference signal 108 is negative in sign and of sufficient magnitude to exceed the low threshold signal.

The difference signal 108 is also coupled to the controller (e.g., control circuit 20), the purpose of which will be described in conjunction with an alternate embodiment of detecting true ventricular fibrillation.

Thus, the first and second comparators together compose a window comparator having the high threshold signal (+THRESHOLD_SET) and the low threshold signal (-THRESHOLD_SET) as reference inputs.

Alternatively, the functions of the first and second comparators 62, 64 may be performed by the controller (described above) in response to the control program. When used, the controller generates the high and low detect 63, 65 signals.

Thus, the high and low threshold signals 66, 68 (200, 202 of FIG. 4) form a window of positive and negative signal magnitudes (204 of FIG. 4) that are sufficiently small enough to not generate the high or low detect signals 63, 65 in the presence of VF waveforms. If the difference signal exceeds the high or low threshold signal in either a positive or negative direction, respectively, a "true R-wave" is present and the high or low 63, 65 detect signal will be generated.

The high and low detect signals 63, 65 are coupled to respective inputs of a two-input "OR" gate 70. If either or both of the high or low detect signals are generated, the "OR" gate 70 generates an event detection signal 71 that signals to other circuits (e.g. the control circuit 20) within the cardiac pacemaker 23, that an R-wave has been detected. The controller (described above) can also perform the functions of the "OR" gate in response to the control program, in which case the detection signal is generated by the controller.

In this way, the present invention accurately detects the presence of true R-waves and does not detect VF waveforms as R-waves. Thus, advantageously, the present invention is immune from generating "false" event detection signals in response to VF waveforms.

Figure 3:
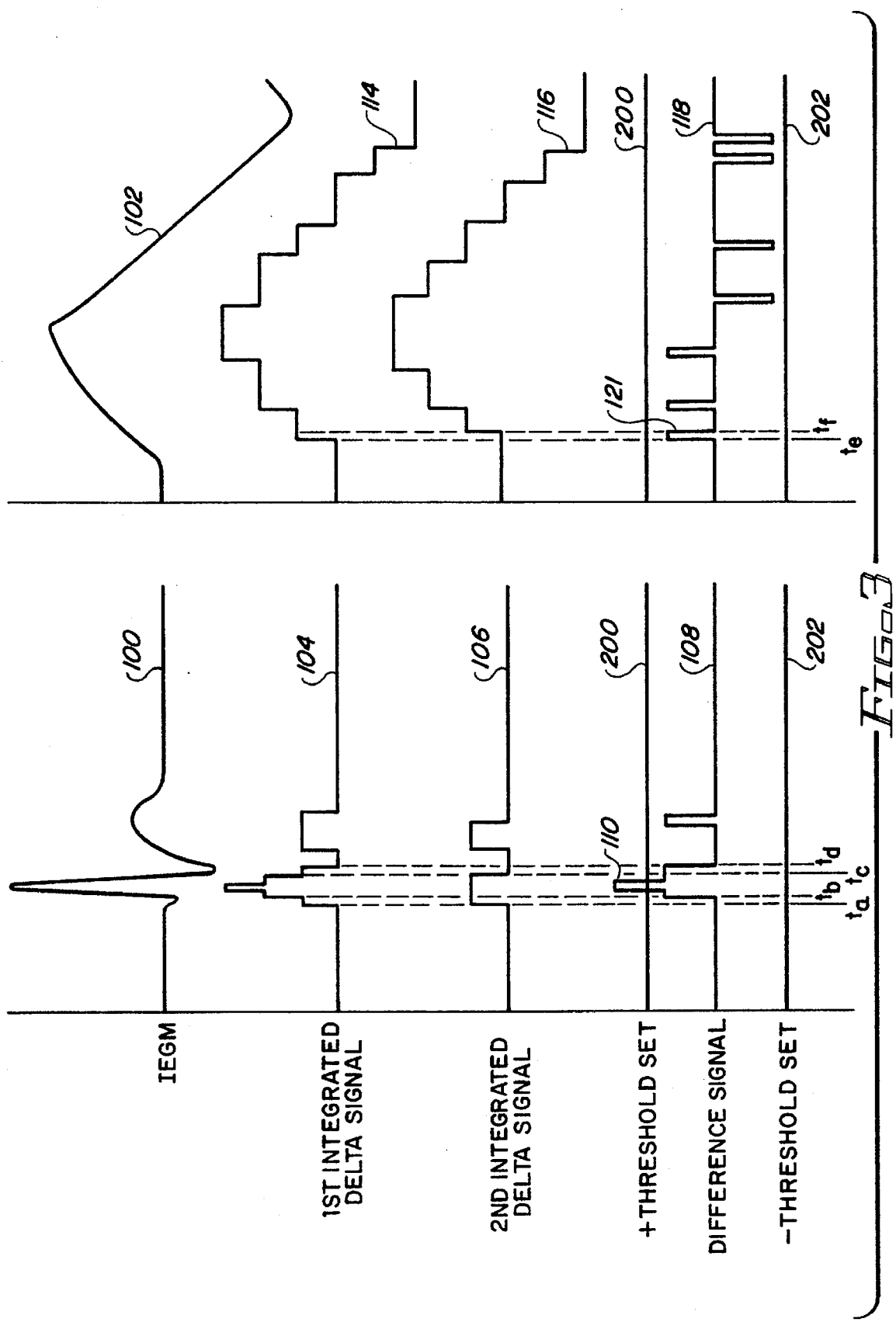
FIG. 3 is a timing diagram showing the various signals generated with the cardiac event detector of FIG. 2.

In FIG. 3, a timing diagram is shown of the various signals generated within the cardiac event detector 21 of the present invention. The R-wave 100 is shown on the left side of FIG. 3, and the VF waveform 102 is shown on the right side of FIG. 3. Below each waveform are various other signals present within the cardiac event detector 21. The first integrated signal 104, and the second integrated signal 106, are shown as generated in response to the R-wave 100. From time $t_a$ to time $t_b$, both of the integrated signals 104, 106 are shown as being equal in magnitude. The difference signal 108 is generated in response to the integrated signals (by the subtractor 60 as described above). From time $t_a$ to time $t_b$, the difference signal is substantially zero in response to the equal integrated signals.

However, because the second integrated signal is generated based on the low-frequency clock signal, it is unable to quickly respond to the steep rise and fall (i.e., high slew rate) of the R-wave 100. Thus, from time $t_c$ to time $t_d$, for example, the integrated signals are not equal, and therefore a non-zero difference signal 108 is generated. Typically, the difference signal will exhibit a peak 110 that exceeds either the high threshold signal 200 or the low threshold 202 signal. As explained above, when the difference signal exceeds either of the threshold signals, the detection signal (not shown) is generated, and thereby signals the occurrence of the R-wave 100 in the IEGM.

The VF waveform 102 similarly causes the generation of the first and second integrated signals 114, 116. However, because the VF waveform has a relatively low slew rate, the low-frequency delta converter is better able respond to the VF waveform 102. As a result, the difference between the first integrated signal 114, and the second integrated signal 116 will be less than it was in response to the R-wave 100. Thus, from time $t_e$ to time tf there is a non-zero difference signal generated 121, but the non-zero difference signal 121 will not be of sufficient magnitude to exceed either the-high or low threshold signal 200, 202. As a result, the detection signal will not be generated in response to the VF waveform 102 being in the IEGM.

Figure 4:
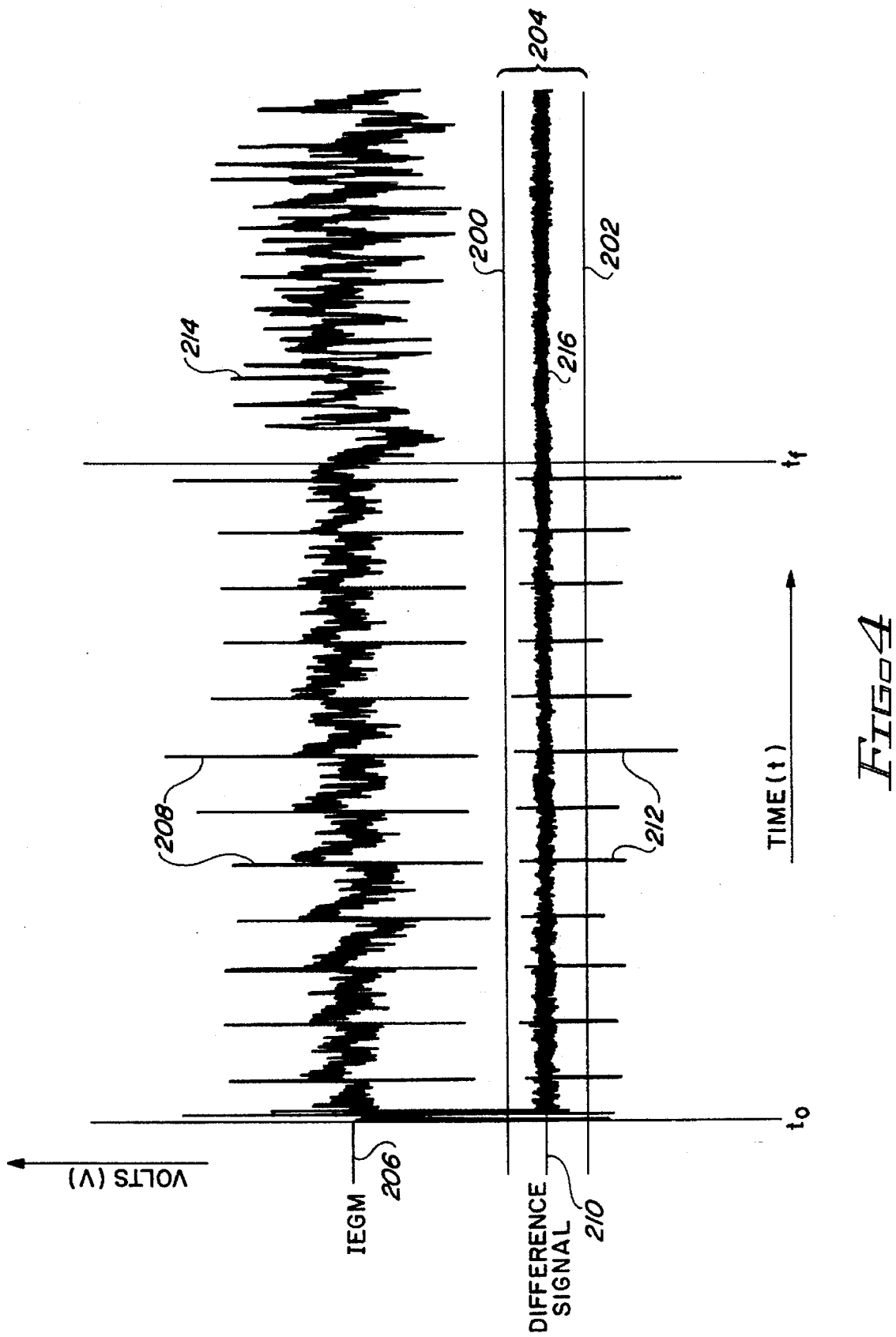
FIG. 4 is graph showing an exemplary intracardiac electrogram (IEGM) signal containing both R-waves, and VF waveforms, and showing a difference signal generated by the event detector of FIG. 2 in response to the exemplary IEGM.

In FIG. 4, a graph is shown of an exemplary IEGM containing both R-waves, and VF waveforms, and showing an exemplary difference signal generated by the embodiment of FIG. 2 in response to the exemplary IEGM.

At time $t_0$ the IEGM from the heart 10 (FIG. 1) is coupled to the device described above through the lead 12 (FIG. 1). The IEGM is represented on an upper horizontal axis 206, wherein voltage is shown as vertical displacement on the graph, and time is shown as horizontal displacement on the graph. From time $t_0$ to time $t_1$ the IEGM contains typical R-waves 208. On a lower horizontal axis 210 the difference signal generated by the subtractor 60 (FIG. 2) is represented, wherein voltage is shown as vertical displacement on the graph, and time is shown as horizontal displacement on the graph. As can be seen, the difference signal voltage exhibits a distinct positive or negative spike 212 (or peak) that corresponds to each of the R-wave peaks in the IEGM on the upper horizontal axis 206. In operation these voltage peaks cause the difference signal to exceed either the high or low threshold signal 200, 202, which in turn cause the generation of the detection signal as described above.

At time $t_1$, the exemplary IEGM ceases to contain typical R-waves 208, and begins to contain ventricular fibrillation (VF) waveforms 214. In response to the VF waveforms 214, the difference signal 216 ceases to exhibit the voltage peaks, instead maintaining a voltage level well within the window of voltages 204 centered around the lower horizontal axis 210. This peak-less signal 216 will not cause the generation of the detection signal.

Thus, advantageously, true R-waves 208 cause the generation of the event detection signal, but the event detection signal is not generated when VF waveforms 214 are present. Thus, the present invention can be characterized as a VF immune R-wave event detector.

In an alternate embodiment, the present invention can be characterized as an improved ventricular fibrillation detector for use in an implantable cardioverter, defibrillator, or a combination device thereof. The present invention defines a non-zero difference signal which occurs in the absence of true R-waves as a reliable indicator of the presence of a VF waveform. Stated differently, VF waveforms are positively indicated when a non-zero difference signal is present that does not exceed either the high or the low threshold signal, as illustrated in FIGS. 3 and 4.

Furthermore, the present invention defines a "zero" difference signal as a quiescent baseline corresponding to the absence of true R-waves. For example, during a systole, no R-waves are generated, and the baseline is quiet. During bradycardia or when the heart is incompetent (and cannot raise its heart rate adequately in response to exercise), R-waves occur at very slow rate. Since VF is not present, the pacemaker senses only a quiescent baseline during its timing cycle. According to the present invention, the delta converters will tract each other and the difference signal will be zero while it samples the quiescent baseline. A zero difference signal is detected by the controller and will indicate to that pacing stimulation, not a shock, is required.

Figure 5:
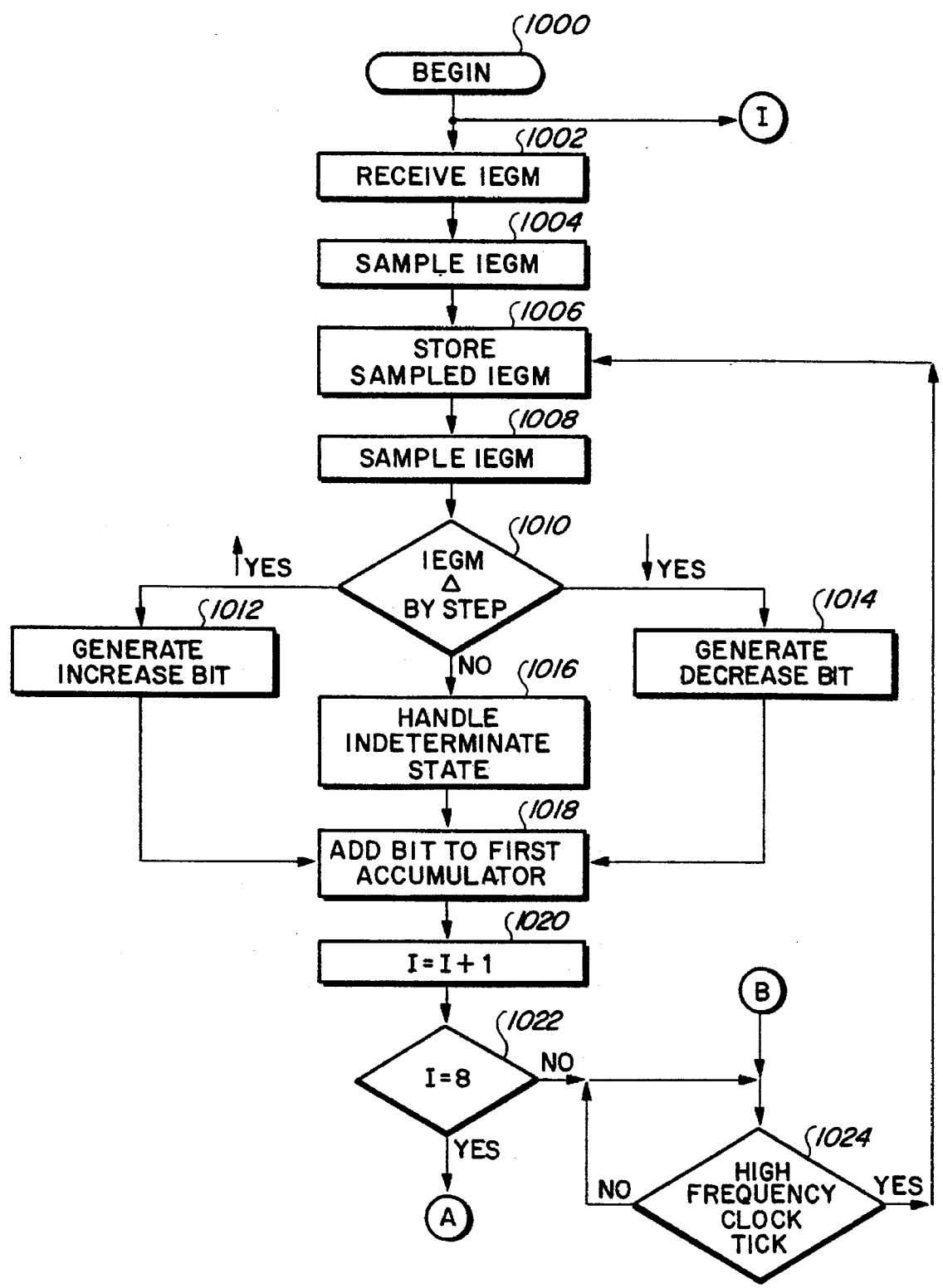
FIGS. 5 and 6 include a flowchart showing the steps traversed by the cardiac event detector for the high-frequency delta converter to produce a first integrated signal.
Figure 6:
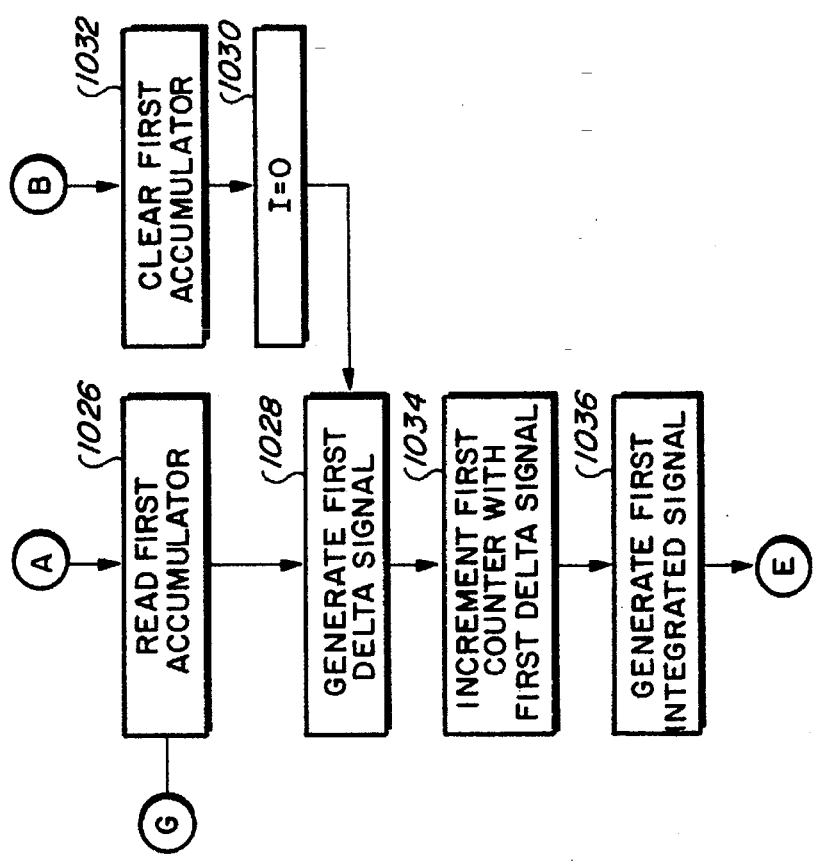

In FIGS. 5 and 6, a flowchart shows the steps traversed by the cardiac event detector 21 (of FIG. 2) for the high-frequency delta converter to produce the first integrated signal. Alternatively, as mentioned above, the steps may instead be partially or completely traversed by a controller in response to a control program.

As shown in FIG. 5, the cardiac event detector 21 begins (block 1000) by receiving the IEGM (block 1002) from the amplifier 30 (FIG. 2). The system is initialized by digitally sampling the IEGM (block 1004), either within the high-frequency delta converter 46, or within the A/D converter (used in conjunction with the controller). The sampled IEGM is stored within the high-frequency delta converter 46, or within a memory that is a part of the controller (block 1006), and a second sample of the IEGM is made (block 1008).

If the current IEGM sample is greater than the previous IEGM sample by at least one step (block 1010), then the increase bit is generated (block 1012), indicating that the IEGM is an increasing signal, by the high-frequency delta converter, or the controller. If the current IEGM sample is less than the previous IEGM sample by at least one step (block 1010), then the decrease bit is generated (block 1014), indicating that the IEGM is a decreasing signal. Finally, if the current IEGM sample does not differ from the previous IEGM sample by more than one step (block 1010), then the high-frequency delta converter, or controller will detect an indeterminate state (block 1016).

The indeterminate state is handled, depending on the particular delta converter or controller/control program used, by generating either the increase bit, the decrease bit or a neutral bit. For example, the high-frequency delta converter 46, or controller, can alternate between generating the increase bit and the decrease bit until the current IEGM sample differs from the previous IEGM sample by more than one step.

In the event either the increase bit or the decrease bit is generated, it will be added to a first accumulator within the high-frequency delta converter 46 or the controller (block 1018). The first accumulator generates an accumulator signal that is indicative of the bits that have been added to the accumulator. The increase bit causes an increase in the accumulator signal, and the decrease bit causes a decrease in the accumulator signal. As a result, the accumulator signal can be either a positive signal (when more increase bits than decrease bits have been added to the accumulator), or a negative signal (when more decrease bits than increase bit have been added to the accumulator). The accumulator signal may, e.g., be a four bit digital signal wherein one of the four bits indicates the sign (positive or negative), and the other three bits indicate the magnitude of the accumulator signal.

Next, a first iteration counter (that is also a part of the high-frequency delta converter, or controller) is incremented (block 1020), and if eight iterations have not recorded within the first iteration counter (block 1022), the high-frequency delta converter, or the controller, waits until the next clock cycle (block 1024), and returns to the step of storing the last IEGM sample (block 1006), and the steps that follow (blocks 1008 through 1022). The clock cycle is generated in response to the high-frequency clock signal described above.

FIG. 6 is a continuation of the flowchart of FIG. 5. After the first iteration counter has recorded eight iterations (block 1022 of FIG. 5), the first accumulator is read (block 1026), and the first delta signal is generated by the high-frequency delta converter, or the controller, in response to the accumulated bits in the first accumulator (block 1028). The first delta signal indicates whether the IEGM was an increasing signal or a decreasing signal, overall, during the delta cycle. Next, the high-frequency delta converter, or controller, clears the first iteration counter (block 1030), clears the first accumulator (block 1032), and waits until the next clock cycle (block 1024 of FIG. 5). The delta converter, or controller, then returns to the step of storing the IEGM signal (block 1006 of FIG. 5), and continues to process (blocks 1006 through 1022 of FIG. 5) as described above.

Also after generating the first delta signal (block 1028), the first counter 56 is incremented in response to the first delta signal (block 1034). Thus, the first counter (or the controller) generates the first integrated signals in response to the first delta signals (blocks 1036).

Figure 8:
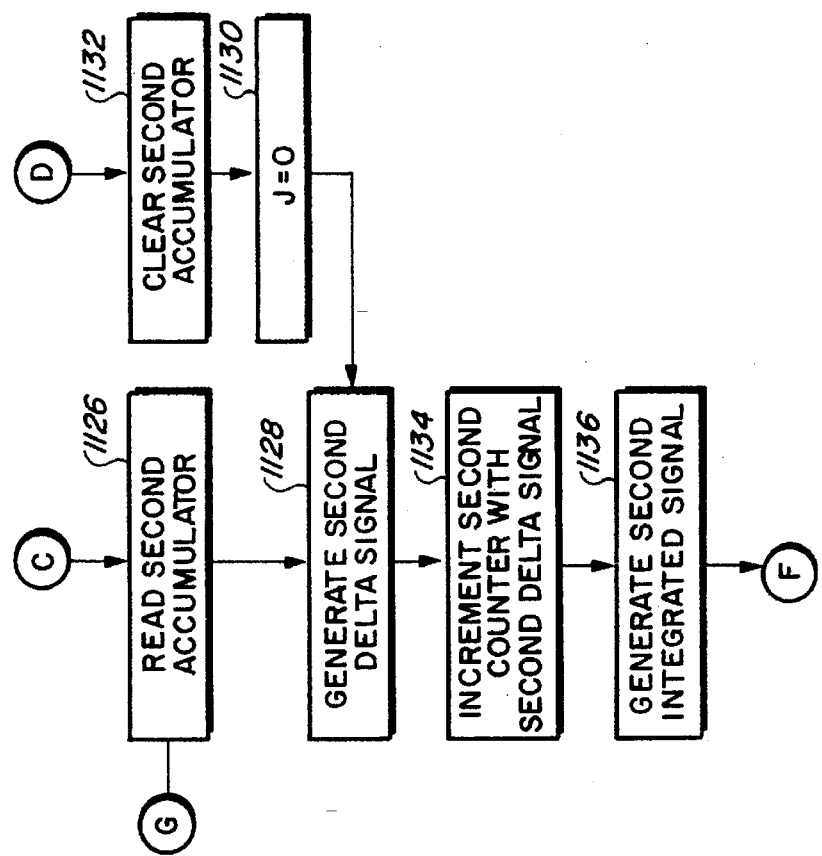
FIGS. 7 and 8 include a flowchart showing the steps traversed by the cardiac event detector for the low-frequency delta converter to produce a second integrated signal.
Figure 7:
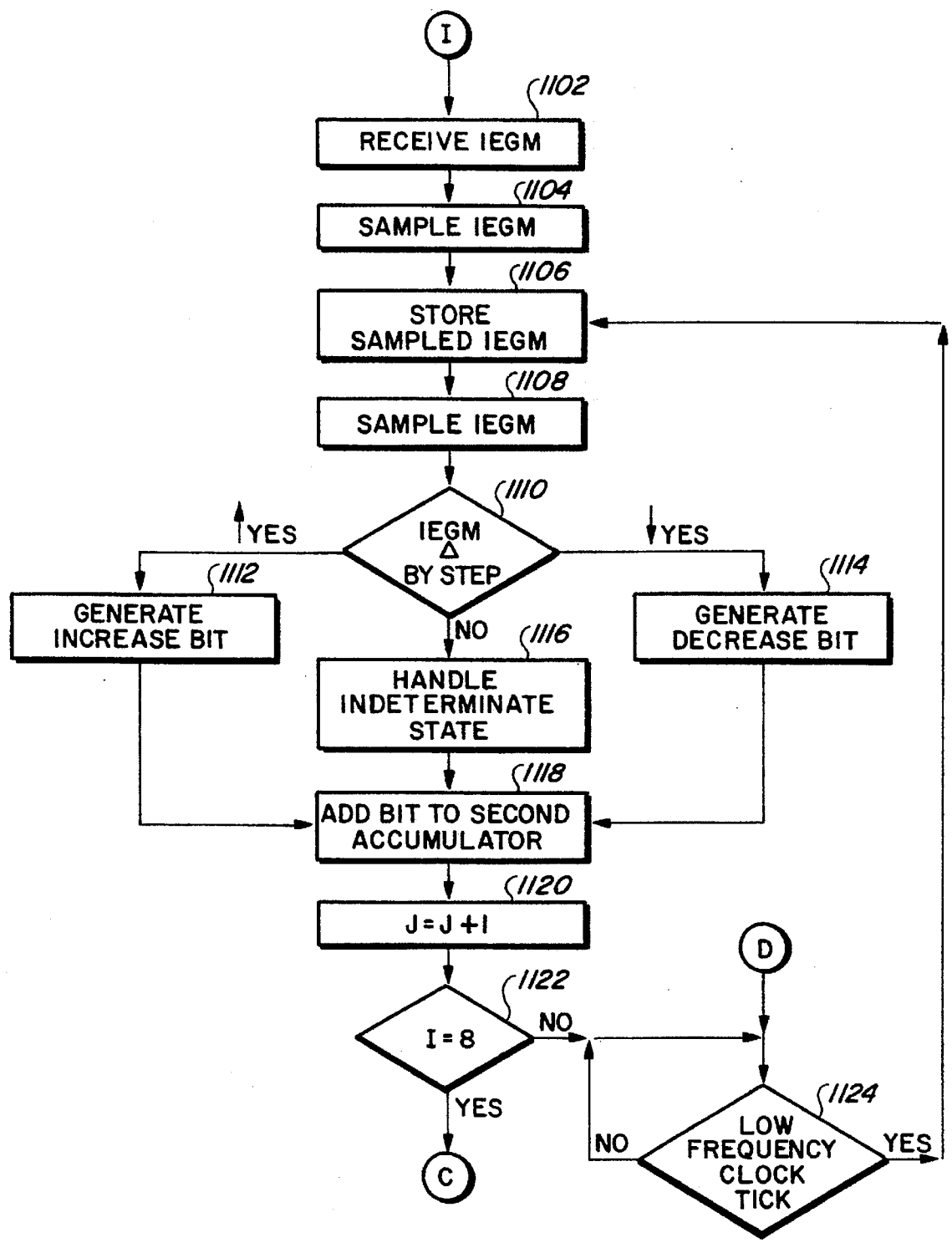

Concurrently with the above described steps, a parallel process is carried out by the low-frequency delta converter, or the controller. As can be seen in FIGS. 7 and 8, the steps traversed by the low-frequency delta converter, or controller, (blocks 1022 through 1134) are substantially the same as the steps traversed by the high-frequency delta converter, described above, except that the low-frequency delta converter utilizes the low-frequency clock signal, and therefore must wait a longer period between clock cycles (block 1124).

As an alternative to using the low-frequency clock signal, the low-frequency delta converter (or controller) may utilize the high-frequency clock signal, but wait for several (e.g., four) clock cycles before repeating steps (blocks 1106 through 1122) similar to those that are repeated by the high-frequency delta converter.

After generating the second delta signal (block 1128), the second counter 58 is incremented in response to the second delta signal (block 1134) that is generated by the low-frequency delta converter 48. Thus, the second counter (or the controller) generates the second integrated signals in response to the second delta signals (blocks 1136).

Figure 9:
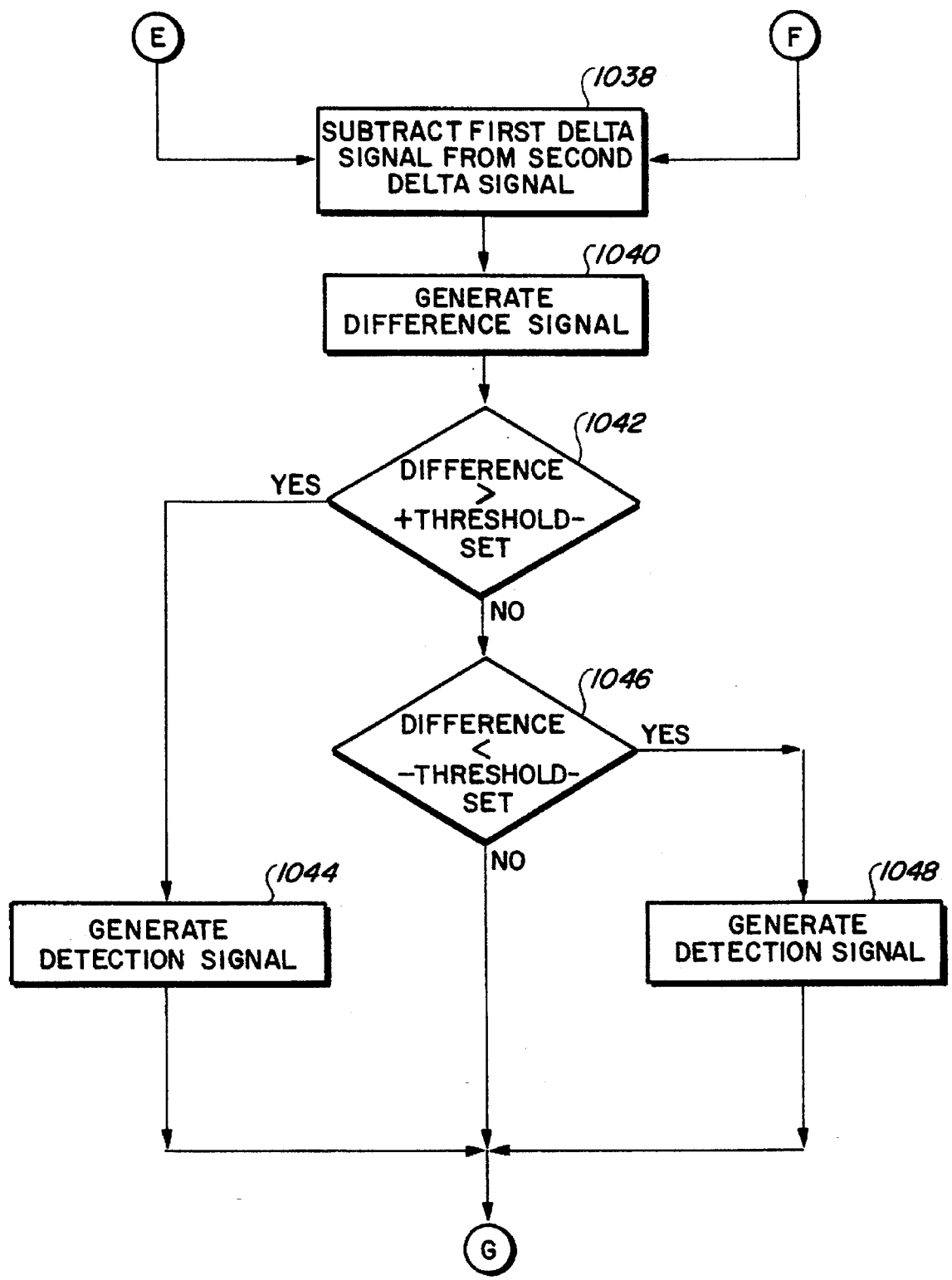
FIG. 9 includes a flowchart showing the steps traversed by the cardiac event detector for determining a difference signal between the first and second integrated signals and, based on a window comparator, produces an event detection signal when one of the threshold voltages is exceeded.

FIG. 9 is a continuation of the flowcharts of FIGS. 6 and 8 which shows the steps traversed by the cardiac event detector 21 for determining the difference signal between the first and second integrated signals and, and produces the event detection signal when one of the threshold voltages is exceeded.

As shown in FIG. 9, the subtractor (or the controller) subtracts the first integrated signal from the second integrated signal (block 1038) and generates the difference signal (block 1040).

The first comparator then compares the difference signal to the high threshold signal (block 1042). In the event that the difference signal exceeds the high threshold signal, the high detect signal is generated, and in response thereto the "OR" gate generates the event detection signal (block 1044).

The difference signal is also compared to the low threshold signal by the second comparator (block 1046), and in the event the difference signal exceeds the low threshold signal, the low detect signal is generated by the second comparator, or controller, and in response thereto the "OR" gate generates the detection signal (block 1048).

Next, the first and second accumulators are again read (blocks 1026, and 1126), and the steps following the reading of the accumulators, described above, are repeated (FIGS. 6, 8 and 9).

In this way, the event detection signal is generated whenever the R-wave is present, and the event detection signal is not generated whenever the VF waveform is present. Ventricular fibrillation may be observed by recognizing that the high speed and low speed delta converters/accumulators contain the same magnitude (within some tolerance).

While the invention herein disclosed has been described by means of specific embodiments and applications thereof, numerous modifications and variations could be made thereto by those skilled in the art without departing from the scope of the invention set forth in the claims.

What is claimed is:

1. An implantable medical device for discriminating R-waves from ventricular fibrillation (VF) waveforms within an intracardiac signal, comprising:

a high-frequency delta converter for receiving the intracardiac signal as an input and for producing as an output a first delta signal, the high-frequency delta converter being responsive to both R-waves and VF waveforms;

a low-frequency delta converter for receiving the intracardiac signal as an input and for producing as an output a second delta signal, the low-frequency delta converter being responsive only to the VF waveforms;

means for determining a difference signal based on the first and second delta signals; and comparator means, coupled to the determining means, for comparing the difference signal to at least one predetermined threshold signal and for producing an event detection signal when the difference signal exceeds the predetermined threshold signal;

whereby an event detection signal is not generated when the VF waveform is present in the intracardiac signal.

2. The implantable medical device of claim 1, wherein the difference determining means comprises:

means for integrating the first delta signal and for producing a first integrated signal thereof;

means for integrating the second delta signal and for producing a second integrated signal thereof; and means for producing the difference signal based on the first and second integrated signals.

3. The implantable medical device of claim 1, wherein the difference determining means comprises:

a first counter that is coupled to the high-frequency delta converter so as to integrate the first delta signal;

a second counter that is coupled to the low-frequency delta converter so as to integrate the second delta signal; and a subtractor that is coupled to the first and second counters, which subtractor generates a difference signal based on the first and second integrated signals.

4. The implantable medical device of claim 1, wherein the at least one predetermined threshold signal includes a high threshold signal and a low threshold signal, and wherein the comparator means comprises:

first detection means for detecting when the difference signal exceeds the high threshold signal, and for producing a high detect signal thereof;

second detection means for detecting when the difference signal exceeds the low threshold signal, and for producing a low detect signal thereof; and means, responsive to the first and second detection means, for generating an event detection signal when one of the high detect signal or the low detect signal is generated.

5. The implantable medical device of claim 1, further comprising:

timing means for generating a high-frequency and a low-frequency clock signal for the high-frequency and the low-frequency delta converters, respectively;

wherein the high-frequency clock signal is at least twice in frequency of the low-frequency clock signal.

6. A method for discriminating R-waves from ventricular fibrillation (VF) waveforms within an intracardiac signal in an implantable medical device, comprising:

tuning a first delta converter to be responsive to both R-waves and VF waveforms;

tuning a second delta converter to be responsive only to VF waveforms;

receiving the intracardiac signal as an input to both the first and the second delta converters and producing as an output a first and a second delta signal, respectively;

determining a difference signal based on the first and second delta signals; and producing an event detection signal whenever the difference signal exceeds at least one predetermined threshold signal;

whereby an event detection signal is not produced when the VF waveform is present in the intracardiac signal.

7. The method of claim 6, wherein the step of determining a difference signal comprises the steps of:

integrating the first delta signal to produce a first integrated signal thereof;

integrating the second delta signal to produce a second integrated signal thereof; and producing the difference signal based on the first and second integrated signals.

8. The method of claim 6, wherein the step of determining a difference signal comprises the steps of:

counting the first delta signal so as to produce a first integrated signal in response to the first delta signal and a high-frequency clock signal;

counting the second delta signal so as to produce a second integrated signal in response to the second delta signal and the high-frequency clock signal; and determining the difference signal between the first and second integrated signals.

9. The method of claim 6, wherein the at least one predetermined threshold signal includes a high threshold signal and a low threshold signal, and wherein the step of producing an event detection signal comprises the steps of:

generating a high detect signal whenever the difference signal exceeds the high threshold signal;

generating a low detect signal whenever the difference signal exceeds the low threshold signal; and generating the event detection signal whenever one of the high detect signal or the low detect signal is generated.

10. The method of claim 6, further comprising:

generating a high-frequency and a low-frequency clock signal, wherein the high-frequency clock signal is at least twice in frequency of the low-frequency clock signal.

11. A method for discriminating R-waves from ventricular fibrillation (VF) waveforms within an intracardiac signal in an implantable medical device, the method comprising the steps of:

(a) receiving an intracardiac signal;

(b) sampling the intracardiac signal using a first delta converter which is responsive to both R-waves and VF waveforms at a first sampling rate;

(c) sampling the intracardiac signal using a second delta converter which is responsive to VF waveforms at a second sampling rate;

(d) determining whether the intracardiac signal, as sampled by the first delta converter, is an increasing signal or a decreasing signal;

(e) determining whether the intracardiac signal, as sampled by the second delta converter, is an increasing signal or a decreasing signal;

(f) evaluating differences between the determination made in step (d) and the determination made in step (e); and (g) generating an event detection signal in response to the evaluation made in step (f) if the differences are of at least one prescribed magnitude.

12. The method of claim 11, wherein the first sampling rate is faster than the second sampling rate, and wherein the determination in step (d) includes the steps of:

(d1) generating an increase bit within the first delta converter in the event the intracardiac signal is an increasing signal, and generating a decrease bit within the first delta converter in the event the intracardiac signal is a decreasing signal;

(d2) accumulating, in the first delta converter, the increase bits and the decrease bits that are generated within the first delta converter;

(d3) repeating steps (d1) and (d2) a prescribed number of times;

(d4) generating, in the first delta converter, a first delta signal that is indicative of the accumulated increase bits and the accumulated decrease bits; and (d5) repeating steps (d3) and (d4) for a first prescribed period of operation.

13. The method of claim 12, and wherein the determination in step (e) includes the steps of:

(e1) generating the increase bit within the second delta converter in the event the intracardiac signal is an increasing signal, and generating the decrease bit within the second delta converter in the event the intracardiac signal is a decreasing signal;

(e2) accumulating, in the second delta converter, the increase bits and the decrease bits that are generated within the second delta converter;

(e3) repeating steps (e1) and (e2) a second prescribed number of times;

(e4) generating, in the second delta converter, a second delta signal that is indicative of the accumulated increase bits and the accumulated decrease bits; and (e5) repeating steps (e3) and (e4) for the prescribed period of operation.

14. The method of claim 13, wherein:

the repeating step (d3) includes the step of waiting for a first prescribed clock cycle before each repetition of steps (d1) and (d2); and the repeating step (e3) includes the step of waiting for a second prescribed clock cycle before each repetition of steps (e1) and (e2).

15. The method of claim 13, wherein the evaluating step (f) includes:

(f1) incrementing a first counter in response to the first delta signal so as to produce a first integrated signal;

(f2) incrementing a second counter in response to the second delta signal so as to produce a second integrated signal; and (f3) determining a difference signal based on the difference between the first integrated signal and the second integrated signal.

16. The method of claim 15, wherein the at least one prescribed magnitude includes a high threshold signal and a low threshold signal, and wherein the generating step (g) includes the steps of:

(g1) generating a high detect signal in the event the difference signal exceeds the high threshold signal;

(g2) generating a low detect signal in the event the difference signal exceeds the low threshold signal; and (g3) generating the event detection signal in response to one of the high detect signal or the low detect signal.

17. The method of claim 13, wherein the generating in step (d1) includes the steps of:

defining an increasing signal within the first delta converter as one that increases by at least a first prescribed step during a clock cycle; and defining a decreasing signal within the first delta converter as one that decreases by at least the first prescribed step during the clock cycle.

18. The method of claim 17, wherein the generating in step (e1) includes the steps of:

defining an increasing signal within the second delta converter as one that increases by at least a second prescribed step during the clock cycle, the second prescribed step being smaller than the first prescribed step; and defining a decreasing signal within the second delta converter as one that decreases by at least the second prescribed step during the clock cycle.

19. The method of claim 11, wherein the first sampling rate is at least twice as fast as the second sampling rate.

20. The method of claim 11, wherein the sampling in step (b) includes the step of:

sampling the intracardiac signal using a first A/D converter.

21. The method of claim 20, wherein the sampling in step (c) includes the step of:

sampling the intracardiac signal using a second A/D converter.

22. The method of claim 21, wherein the determining step (d) includes the steps of:

(d1) generating an increase bit within a controller when the intracardiac signal is an increasing signal, and generating a decrease bit within the controller when the intracardiac signal is a decreasing signal;

(d2) accumulating the increase bits and the decrease bits in a first accumulator within the controller;

(d3) repeating steps (d1) and (d2) a prescribed number of times;

(d4) generating a first delta signal that is indicative of the accumulated increase bits and the accumulated decrease bits in the first accumulator; and (d5) repeating steps (d3) and (d4) for a prescribed period of operation.

23. The method of claim 22, wherein the determining step (e) includes the steps of:

(e1) generating the increase bit within the controller when the intracardiac signal is an increasing signal, and generating the decrease bit within the controller when the intracardiac signal is a decreasing signal;

(e2) accumulating the increase bits and the decrease bits in a second accumulator within the controller;

(e3) repeating steps (e1) and (e2) a prescribed number of times;

(e4) generating a first delta signal that is indicative of the accumulated increase bits and the accumulated decrease bits in the second accumulator; and (e5) repeating steps (e3) and (e4) for a prescribed period of operation.

24. The method of claim 23, wherein:

the repeating step (d3) includes the step of waiting for at least one prescribed clock cycle before each repetition of steps (d1) and (d2); and the repeating step (e3) includes the step of waiting for more than the at least one prescribed clock cycle before each repetition of steps (e1) and (e2).

25. The method of claim 24, wherein the evaluating step (f) includes the steps of:

(f1) incrementing a first counter within the controller in response to the first delta signal so as to produce a first integrated signal;

(f2) incrementing a second counter within the controller in response to the second delta signal so as to produce a second integrated signal; and (f3) determining a difference signal based on the difference between the first integrated signal and the second integrated signal.

26. The method of claim 25, wherein the at least one prescribed magnitude includes a high threshold signal and a low threshold signal, and wherein the generating step (g) includes the steps of:

(g1) generating a high detect signal when the difference signal exceeds the high threshold signal;

(g2) generating a low detect signal when the difference signal exceeds the low threshold signal; and (g3) generating the event detection signal in response to one of the high detect signal or the low detect signal.

27. The method of claim 23, wherein:

the repeating step (d3) includes the steps of waiting for a first prescribed clock cycle before each repetition of steps (d1) and (d2); and the repeating step (e3) includes the steps of waiting for a second prescribed clock cycle before each repetition of steps (e1) and (e2).

28. A method for detecting a R-wave in a intracardiac signal, wherein the method is immune from detecting the R-wave in response to ventricular fibrillation waveforms present in the intracardiac signal, the method comprising the steps of:

(a) converting the intracardiac signal to a first delta signal such that high-frequency signals are accurately sampled;

(b) converting the intracardiac signal to a second delta signal such that low-frequency signals are accurately sampled;

(c) incrementing a first counter means in response to the first delta signal so as to generate a first count;

(d) incrementing a second counter means in response to the second delta signal so as to generate a second count;

(e) determining a difference signal based on the first and second counts;

(f) comparing the difference signal to a predetermined high threshold signal using first comparison means that generates a high detect signal when the difference signal exceeds the predetermined high threshold signal;

(g) comparing the difference signal to a predetermined low threshold signal using second comparison means that generates a low detect signal in response to the difference signal exceeding the predetermined low threshold signal; and (h) producing an event detection signal, indicative of a true R-wave, whenever the difference signal exceeds one of the high or low threshold signal, wherein the absence of an event detection signal indicates that ventricular fibrillation is present since the high-frequency and low-frequency delta converters produce first and second delta signals of approximately the same magnitude.

29. The method of claim 28, wherein:

the converting step (a) includes the step of converting the intracardiac signal to a first delta signal using a high-frequency delta converter that is clocked by a high-frequency clock signal; and the converting step (b) includes the step of converting the intracardiac signal to a second delta signal using a low-frequency delta converter that is clocked by a low-frequency clock signal.

30. An implantable medical device for detecting a true R-wave, and for not detecting a false R-wave when a ventricular fibrillation waveform is present, the implantable medical device comprising:

a high-frequency delta converter having means for receiving an intracardiac signal as an input and coupled to a high-frequency clock signal, which high-frequency delta converter generates a first delta signal in response to the intracardiac signal and the high-frequency clock signal;

a low-frequency delta converter also adapted to receive the intracardiac signal and coupled to a low-frequency clock signal, which low-frequency delta converter generates a second delta signal in response to the intracardiac signal and the low-frequency clock signal;

means for integrating the first delta signal;

means for integrating the second delta signal;

means for generating a difference signal that is indicative of the difference between the first and second integrated signals;

means for generating a high threshold signal and a low threshold signal;

means for comparing the difference signal to the high threshold signal, and for generating a high detect signal in the event that the difference signal exceeds the high threshold signal;

means for comparing the difference signal to the low threshold signal, and for generating a low detect signal in the event that the difference signal exceeds the low threshold signal; and event detection means for producing an event detection signal when the high detect signal or the low detect signal is generated, wherein the absence of an event detection signal indicates that ventricular fibrillation is present since the first and second integrated signals of a ventricular fibrillation waveform have approximately the same magnitude;

whereby the event detection signal is generated when true R-waves are present in the intracardiac signal.

31. The implantable medical device of claim 30, wherein the frequency of the high-frequency clock signal is at least twice the frequency of the low-frequency clock signal.

32. An implantable medical device for detecting a true R-wave in an IEGM, and for not detecting a false R-wave in response to a VF waveform, the implantable medical device comprising:

means for receiving the intracardiac signal;

means for sampling the intracardiac signal at a first sampling rate, and for generating a first sampled signal in response to such sampling;

means for sampling the intracardiac signal at a second sampling rate, and for generating a second sampled signal in response to such sampling;

means for detecting whether the first sampled signal is an increasing signal or a decreasing signal, and for generating a first detection signal in response to such detection;

means for detecting whether the second sampled signal is an increasing signal or a decreasing signal, and for generating a second detection signal in response to such detection;

means evaluating differences between the first detection signal and the second detection signal, and for generating an evaluation signal in response to such evaluation; and means generating a detection signal in response to the evaluation signal if the differences are of at least a prescribed magnitude.

33. An implantable medical device, comprising:

lead delivery means for receiving cardiac signals and transmitting stimulation pulses to a patient's heart;

sensing means for sensing true R-waves, the sensing means including:

first conversion means, responsive to both R-waves and VF waveforms, for producing a first converted signal;

second conversion means, responsive only to the VF waveforms, for producing a second converted signal;

means for determining a difference signal based on the first and second converted signals; and event detection means, coupled to the determining means, for detecting true R-waves when the difference signal exceeds a predetermined threshold signal;

means for detecting a non-zero difference signal that does not exceed the predetermined threshold signal corresponding to a VF waveform;

shock generating means for generating shocking pulses to the heart when a VF waveform is detected;

whereby an event detection signal is not generated when the VF waveform is present in the intracardiac signal.

34. The implantable medical device of claim 33, wherein:

the first conversion means corresponds to a first delta converter; and the second conversion means corresponds to a second delta converter.

35. The implantable medical device of claim 33, wherein:

the first conversion means corresponds to a first A/D converter; and the second conversion means corresponds to a second A/D converter.

36. An implantable medical device, comprising:

lead delivery means for receiving cardiac signals and transmitting stimulation pulses to a patient's heart;

sensing means for sensing true R-waves, the sensing means including:

first conversion means, responsive to both R-waves and VF waveforms, for producing a first converted signal;

second conversion means, responsive only to the VF waveforms, for producing a second converted signal;

means for determining a difference signal based on the first and second converted signals; and detection means, coupled to the determining means, for detecting true R-wave when the difference signal exceeds a predetermined threshold signal, for detecting VF waveforms when a non-zero difference signal does not exceed the predetermined threshold signal, and for detecting an absence on true R-waves corresponding to asystole when a zero difference signal is detected;

pulse generating means for generating stimulation pulses in the absence of true R-waves;

inhibiting means for inhibiting the pulse generating means when true R-waves are detected; and shock generating means for generating shocking pulses to the heart when a VF waveform is detected;

whereby an event detection signal is not generated when the VF waveform is present in the intracardiac signal.

37. The implantable medical device of claim 36, wherein:

the first conversion means corresponds to a first delta converter; and the second conversion means corresponds to a second delta converter.

38. The implantable medical device of claim 36, wherein:

the first conversion means corresponds to a first A/D converter; and the second conversion means corresponds to a second A/D converter.

* * * * *